(12) United States Patent
Hanelt et al.

(10) Patent No.: US 6,486,338 B1
(45) Date of Patent: Nov. 26, 2002

(54) PREPARATION OF ORGANOSILICON COMPOUNDS CONTAINING α, β-UNSATURATED CARBOXYLIC ACIDS

(75) Inventors: Eckhard Hanelt, Geltendorf (DE); Frank Sandmeyer, Burghausen (DE); Norman Häberle, Müchen (DE); Wolfram Schindler, Unterhaching (DE)

(73) Assignee: Consortium fur Elektrochemische Industrie GmbH, Munich (DE)

( * ) Notice: Subject to any disclaimer, the term of this patent is extended or adjusted under 35 U.S.C. 154(b) by 0 days.

(21) Appl. No.: 09/491,034

(22) Filed: Jan. 25, 2000

(30) Foreign Application Priority Data

Jan. 28, 1999 (DE) .......................................... 199 03 333

(51) Int. Cl.⁷ .................................................. C02F 7/08
(52) U.S. Cl. ...................................... 556/438; 556/440
(58) Field of Search ................................. 556/438, 440

(56) References Cited

U.S. PATENT DOCUMENTS

| | | |
|---|---|---|
| 4,859,031 A | 8/1989 | Berman et al. |
| 4,996,330 A | 2/1991 | Scherowsky et al. |
| 5,211,877 A | 5/1993 | Andrejewski et al. |
| 5,214,077 A | 5/1993 | Herzig et al. |
| 5,362,315 A | 11/1994 | Muller-Rees et al. |
| 5,502,206 A | 3/1996 | Zahn et al. |
| 5,506,704 A | 4/1996 | Broer et al. |
| 5,599,412 A | 2/1997 | Faris |
| 5,610,258 A | 3/1997 | Weitzel et al. |
| 5,682,212 A | 10/1997 | Maurer et al. |
| 5,683,622 A | 11/1997 | Kratzschmar et al. |
| 5,691,789 A | 11/1997 | Li et al. |
| 5,695,680 A | 12/1997 | Weitzel et al. |

FOREIGN PATENT DOCUMENTS

| | | |
|---|---|---|
| DE | 43 42 280 A1 | 6/1995 |
| DE | 44 08 171 A1 | 9/1995 |
| DE | 195 41 838 A1 | 5/1997 |
| DE | 196 19 460 A1 | 11/1997 |
| DE | 198 33 258 C1 | 10/1999 |
| EP | 0 110 370 B1 | 4/1987 |
| EP | 0 724 005 A2 | 7/1996 |

OTHER PUBLICATIONS

The English Derwent Abstract AN 1995–216450 (29) corresponding to DE 4342280 is enclosed.
The English Derwent Abstract AN 1996–343521 (35) corresponding to EP 724005 is enclosed.
The English Derwent Abstract AN 1997–118995 (11) corresponding to DE 19541838 is enclosed.
The English Derwent Abstract AN 1995–321444 (42) corresponding to DE 4408171 is enclosed.
The English Derwent Abstract AN 1998–000705 (01) corresponding to DE 19619460 is enclosed.
H. Finkelmann, H. Ringsdorf et al.; Synthesis of Cholesteric Liquid Crystalline Polymers; No. 179; pp. 829–832; (1978).
Derwent Abstract Corresponding To DE–C 198 33 258 (AN 1988–065213).
International Search Report—May 22, 2000.

*Primary Examiner*—Paul F. Shaver
(74) *Attorney, Agent, or Firm*—Brooks & Kushman P.C.

(57) ABSTRACT

Organosilicon compounds (P) containing α,β-unsaturated carboxylic acid radicals, of the general formula (1)

$$-A-O-C(O)-CR=CH_2 \qquad (1),$$

are prepared by a process in which, in a first step, organosilicon compounds (H) containing hydrogen atoms bonded directly to silicon are reacted with olefinically unsaturated compounds (U) containing a terminal double or triple bond, of the general formula (2)

$$\Omega-O-C(O)-CRH-CH_2-Z \qquad (2),$$

in the presence of metals or compounds from the platinum group as catalyst, to give organosilicon compounds (E) containing radicals of the general formula (3)

$$-A-O-C(O)-CRH-CH_2-Z \qquad (3),$$

and, in a second step, H—Z compounds are eliminated from organosilicon compounds (E), where A is a divalent organic radical,
Ω is a monovalent organic radical containing a terminal double or triple bond,
R is an H atom or a methyl radical, and
Z is Cl, I, Br or 4-methyltoluenesulfonyl.

19 Claims, No Drawings

PREPARATION OF ORGANOSILICON COMPOUNDS CONTAINING α, β-UNSATURATED CARBOXYLIC ACIDS

TECHNICAL FIELD

The present invention relates to a process for the preparation of organosilicon compounds (P) containing α,β-unsaturated carboxylic acid radicals, to polymers of the organosilicon compounds (P), to compositions comprising organosilicon compounds (P), and to optically anisotropic layers produced by alignment and polymerization of liquid-crystalline organosilicon compounds (P).

BACKGROUND ART

The syntheses and applications of crosslinkable organosiloxanes and organosilanes, in particular siloxanes and silanes containing methacryloyl groups, are described in large number in the literature. Frequently used materials, which are, for example, employed for coatings, are alkoxy-substituted silanes, which, besides the methacryloyl groups, usually also contain methoxy or ethoxy groups. Owing to the relatively low reactivity of the methacryloyl groups, however, the crosslinking density of the polymerized layers produced from these compounds is comparatively low. In many applications, an increase in the crosslinking density could produce better material properties, for example an improvement in the solvent stability, an improvement in the adhesion to the surfaces to be coated, or an increase in the hardness of the coatings. Possible solutions to the preparation of highly crosslinked structures of this type are to increase the number of polymerizable groups, and to use polymerizable groups of higher reactivity than that of the methacryloyl groups, for example acryloyl groups. However, the processes disclosed hitherto for the preparation of such organosiloxanes and organosilanes containing polymerizable groups of high reactivity can only be carried out with difficulty on an industrial scale, or do not give the desired result for reasons associated with the method of production. This is particularly true in the case of acryloyl groups.

It is known that crosslinked organosiloxanes having a liquid-crystalline structure are frequently insufficiently stable to external influences, such as exposure to certain organic solvents. U.S. Pat. No. 5,362,315 discloses, for example, pigments comprising liquid crystalline substances having a chiral phase which are distinguished by the fact that their color depends on the viewing angle. These pigments are employed in various transparent media, such as coatings, binders or plastics. However, EP-A-724005 discloses that when these pigments are prepared from liquid-crystalline organosiloxanes in which the polymerizable groups are exclusively methacryloyl groups, they then, depending on the processing conditions and the medium into which the pigments are incorporated, exhibit color changes which cannot be tolerated in a large number of applications. A solution to this problem, or at least a reduction in its magnitude, can likewise be achieved by increasing the network density of the aligned and crosslinked liquid-crystalline structure.

Various methods are known for the preparation of organosiloxanes and silanes containing methacryloyl groups. A process which is frequently used on an industrial scale comprises the hydrosilylation of di-unsaturated compounds containing double or triple bonds of different reactivity. The aim in this process is for an ω-olefinically unsaturated group to be the target of Si—H attack, while the second unsaturated group is not hydrosilylated. To this end, the reactivity of the group which is not to be hydrosilylated must be lower than the reactivity of the other unsaturated groups. The unsaturated group of lower reactivity is preferably the methacryloyl double bond, but, in principle, the methacryloyl double bond can also be hydrosilylated. In general, more than 10% of side-reactions of methacryloyl groups with Si—H groups take place, the proportion of these side-reactions corresponding to the concentration of the methacryloyl double bonds. In general, the competing hydrosilylation of the two different unsaturated systems thus necessitates that undesired byproducts, for example, dimers, are always produced in such processes, in a proportion which generally depends on the nature of the unsaturated groups and on the manner in which the reaction is carried out.

If the polymerizable groups to be used are α,β-unsaturated carboxylic acid radicals of relatively high reactivity, such as, for example, the acryloyl double bond, the competition with ω-olefinically unsaturated groups is significantly higher than in the case of methacryloyl double bonds under the conditions of the hydrosilylation reaction. Organosiloxanes or silanes containing acryloyl groups are therefore not readily accessible in the manner described above, since the high proportion of side-reactions results in partial crosslinking even during the hydrosilylation reaction, or in the case of siloxanes or silanes containing only one hydrogen atom bonded directly to silicon, in double addition of the siloxane or silane moiety to the di-unsaturated compound. If the organosiloxanes contain mesogenic side groups, the consequent increase in the viscosity usually reduces the mobility of the mesogens so much that a uniformly aligned liquid-crystalline phase can form only with difficulty, if at all.

U.S. Pat. No. 5,211,877 therefore describes, as an alternative method for the preparation of liquid-crystalline organosiloxanes or silanes containing methacryloyl or acryloyl groups, a multistep synthesis in which the methacryloyl or acryloyl group is introduced subsequently, by esterification using a reactive methacryloyl or acryloyl compound after hydrosilylation of a precursor containing a hydroxyl group protected by a protecting group, and subsequent removal of the protecting group. Owing to the large number of reaction steps necessary, however, this method tends to be more practicable for small laboratory syntheses. It is unsuitable for the production of highly crosslinkable organosiloxanes and organosilanes on an industrial scale.

DISCLOSURE OF INVENTION

An object of the present invention is to provide a process which can be implemented on an industrial scale for the preparation of crosslinkable organosilicon compounds containing α,β-unsaturated carboxylic acid radicals in high selectivity.

BEST MODE FOR CARRYING OUT THE INVENTION

The invention relates to a process for the preparation of organosilicon compounds (P) containing α,β-unsaturated carboxylic acid radicals, of the general formula (1)

in which, in a first step,
organosilicon compounds (H) containing hydrogen atoms bonded directly to silicon are reacted with olefinically unsaturated compounds (U) containing a terminal double or triple bond, of the general formula (2)

$$\Omega\text{-O}—C(O)—CRH—CH_2—Z \quad (2),$$

in the presence of metals or compounds from the platinum group as catalyst, to give organosilicon compounds (E) containing radicals of the general formula (3)

$$—A—O—C(O)—CRH—CH_2—Z \quad (3),$$

and, in a second step, H—Z compounds are eliminated from organosilicon compounds (E), where A is a divalent organic radical, $\Omega$ is a monovalent organic radical containing a terminal double or triple bond, R is an H atom or a methyl radical, and Z is Cl, I, Br or 4-methyltoluenesulfonyl.

The process proceeds in high selectivity in both steps and therefore gives very pure organosilicon compounds (P) since the undesired hydrosilylation of the α,β-unsaturated radical —CR=CH$_2$ in the general formula (1), and premature polymerizations caused thereby, are avoided.

The elimination of the H—Z compounds is preferably carried out by means of a base, such as a tertiary amine, for example triethylamine or tributylamine, or a basic metal salt of an acid, such as, for example, $K_2CO_3$, $Na_2CO_3$, $KHCO_3$, $NaHCO_3$, Na acetate and $KOC(O)C(CH_3)=CH_2$. The H—Z compound is then chemically bound to the base as a salt.

The organosilicon compounds (H) employed are, in particular, organosiloxanes, which may be linear, branched, or crosslinked organosiloxanes, or which may be in the form of organosilsesquioxanes, or organosilanes.

The organosiloxanes (H) employed are preferably built up from at least 2 identical or different units of the general formula (4)

$$[H_pR'_qSiO_{(4-p-q)/2}] \quad (4),$$

in which $R^1$ is a $C_1$- to $C_{10}$-alkyl or phenyl radical which is unsubstituted or substituted by halogen atoms, and p and q each have the value 0, 1, 2 or 3, where the sum of p and q is at most 3, and in at least one unit per molecule, p has the value 1, 2 or 3.

The organosiloxanes (H) are preferably built up from 2 to 30 units, in particular 2 to 15 units, of the general formula (4). The subscripts p and q preferably each have the value 1 in at least 30% of all units of the general formula (4). Preferred radicals $R^1$ are methyl radicals. Particularly preferred siloxanes of the general formula (4) are cyclotetrasiloxanes, cyclopentasiloxanes, tetramethyldisiloxanes and linear polymethylsiloxanes preferably having from 4 to 15 silicon atoms and trimethylsilyl groups as end groups.

The organosilanes (H) employed preferably have the general formula (5)

$$H_sSiR^2_t \quad (5),$$

in which $R^2$ is a halogen atom or a $C_1$- to $C_{10}$-alkyl or phenyl radical which is unsubstituted or substituted by halogen atoms, s has the value 1, 2, 3 or 4, and t has the value 0, 1, 2, 3 or 4, where the sum of s and t is at most 4.

The subscript s preferably has the value 1 or 2. Particularly preferred silanes of the general formula (5) are those which contain radicals $R^2$ which are either all identical and are each a chlorine atom, or are different and are a combination of one or two halogen atoms and $C_1$–$C_4$-alkyl radicals or phenyl radicals.

Preference is given to compounds (U) in which, in the general formula (2), $\Omega$ is $R^3$—$A^0$, where $R^3$ is a monovalent radical of the formula $CH_2=CH—(CH_2)_n$ or $HC\equiv C—(CH_2)_n$, in which n is an integer having a value of from 0 to 8, and in which one or more non-adjacent methylene units may be replaced by oxygen atoms or dimethylsilyl radicals, and $A^0$ is a chemical bond or a divalent organic radical.

$A^0$ can be prepared by known processes of synthetic organic chemistry. A hydrosilylatable group can be bonded to $A^0$ by known chemical reactions, such as esterification, condensation, etherification, alkylation, alkenylation, alkynylation or acylation. $A^0$ may additionally be capable of forming an ester bond by virtue of the organic radical $A^0$ being bonded to the divalent oxygen atom of an ester carbonyloxy group.

In a preferred embodiment, the first process step is carried out using compounds (U) in which $A^0$ is $(CRH)_m$—, where m is an integer having a value of from 0 to 12, and R is an H atom or a methyl radical, and where one or more non-adjacent methylene units may be replaced by oxygen atoms, dimethylsilyl radicals, 1,4-substituted phenylene, or cyclohexylene units. The organosiloxanes (P) prepared therefrom are particularly suitable for the production of highly crosslinked coatings and as additives for surface-coating preparations.

In order to prepare liquid-crystalline organosiloxanes (P), mesogenic compounds are hydrosilylated onto the organosilicon compounds (H) in this process.

In a preferred embodiment, polymerizable liquid-crystalline organosiloxanes (P) are prepared. To this end, use may be made, in a first process step, of mesogenic compounds, preferably selected from compounds of the general formula (6)

$$R^3—X^1—(A^1—X^2)_d—R^5—O—C(O)—CH(R)—CH_2—Z \quad (6)$$

and compounds of the general formula (7)

$$R^3—X^1—(A^1—X^2)_d—R^5—A^2 \quad (7),$$

where $R^3$, R and Z are as defined above, $R^5$ is a chemical bond or a radical of the formula $(CH_2)_m$, in which m is an integer having a value of from 1 to 12, and in which one or more non-adjacent methylene units may be replaced by oxygen atoms or dimethylsilyl radicals, $X^1$ is selected from a chemical bond and the divalent radicals —O—, —C(O)O— and —OC(O)—, $X^2$ is a binding member selected from a chemical bond and the divalent radicals —C(O)O—, —OC(O)—, —CH$_2$CH$_2$—, —CH=N—, —N=CH—, —N=N—, —C(O)NH—, —NHC(O)—, —C≡C—, —CH=CH—, —N=N(O)— and —N(O)=N—, $A^1$ is a divalent radical selected from six-membered homocyclic or heterocyclic rings, such as 1,4-phenylene, 1,4-cyclohexylene, 2,5-pyridinylene, 2,5-pyranylene, 2,5-pyrimidinylene, 5,2-pyrimidinylene, 2,5-(1,3-dioxanylene) and 5,2-(1,3-dioxanylene), which are unsubstituted or substituted by cyano, fluorine or methyl groups, or from bicyclic compounds consisting of six-membered rings, such as 2,6-naphthylidene, 2,7-naphthylidene and 1,4-naphthylidene, $A^2$ is an end group selected from hydrogen, halogen, hydroxyl, nitrile, methacryloyloxy, methacryloylethyleneoxy, cholestane, cholesteryl, doristeryl, monofunctional dianhydrohexitol, cyclohexyl and alkenyl radicals having 1 to 10 carbon atoms, in which one or more non-adjacent methylene units may be replaced by oxygen atoms or dimethylsilyl radicals, and d can have the value 2 or 3.

Preferably, at least 5% of the radicals of the organosiloxanes (P) are prepared by hydrosilylation using compounds selected from mesogenic compounds of the general formula (6) and compounds of the general formula (2) in which $A^0$ is a chemical bond or a divalent organic radical of the above formula $(CRH)_m$—.

Preferably, at least 20% of the radicals of the organosiloxanes (P) are mesogenic radicals. The term "mesogenic radicals" is taken to mean groups which can produce liquid-crystalline properties in a molecule. A regularly updated collection of known mesogenic groups is published by V. Vill et al. as a database entitled LiqCryst (can be purchased from LCI Publisher GmbH, Eichenstr. 3, D-20259 Hamburg).

It has been found that the introduction of the —C(O)O— or —OC(O)— groups as radicals $X^2$ favorably affects the formation of homogeneous liquid-crystalline phases. These radicals are therefore preferred.

Preferred mesogenic compounds (U) of the general formula (6) are the compounds (U) of the general formula (8)

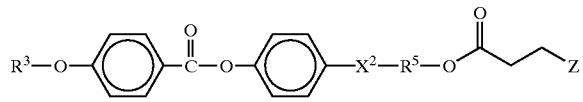

(8)

where $X^2$, $R^5$ and Z are as defined for the general formula (6).

In the particularly preferred compounds (U) of the general formula (8), $X^2$ are selected from a chemical bond and divalent radicals from the group consisting of —C(O)O— and —OC(O)—, $R^5$ are selected from a chemical bond and $C_1$- to $C_6$-alkyl radicals, and Z is a chlorine atom. $R^3$ is preferably a $CH_2$ =CH—$CH_2$— group.

In the hydrosilylation, the organosiloxanes (H) containing hydrogen atoms bonded directly to silicon, which are preferably built up from units of the general formula (4) or (5), are reacted simultaneously or successively with a freely adjustable mixture of olefinically unsaturated compounds (U) containing terminal double or triple bonds, of the general formula (2), in the presence of, preferably, at least one metal from the platinum group and/or compounds thereof, where the total number of moles of the olefinically unsaturated compounds (U) corresponds to the total number of Si—H bonds in the organosiloxanes (H), or, in order to ensure complete saturation, an excess of one of the two components (H) and (U) of up to 20% is initially introduced. Suitable hydrosilylation processes are described, for example, in U.S. Pat. No. 5,211,877, U.S. Pat. No. 5,214,077 and DE-A-19541838.

Examples of metals from the platinum group and/or compounds thereof—referred to below as platinum catalyst—which can be employed in the process according to the invention are platinum, palladium, rhodium, iridium and compounds thereof, preferably platinum and/or compounds thereof. It is possible to employ all catalysts which have also been employed hitherto for the addition reaction of hydrogen atoms bonded directly to Si atoms onto aliphatically unsaturated compounds. Examples of such catalysts are metallic and finely divided platinum, which can also be on supports such as silicon dioxide, aluminum oxide or activated carbon, compounds or complexes of platinum such as platinum halides, for example $PtCl_4$, $H_2PtCl_6.6\ H_2O$, $Na_2PtCl_4.4\ H_2O$; platinum-olefin complexes, platinum-alcohol complexes, platinum-alkoxide complexes, platinum-ether complexes, platinum-aldehyde complexes, platinum-ketone complexes, including products of the reaction of $H_2PtCl_6.6H_2O$ and cyclohexanone, platinum-vinylsiloxane complexes, in particular platinum-divinyltetramethyldisiloxane complexes with or without a content of detectable inorganically bound halogen, bis (gamma-picolinyl)platinum dichloride, trimethylenedipyridinylplatinum dichloride, dicyclopentadienylplatinum dichloride, (dimethyl sulfoxide)ethyleneplatinum(II) dichloride and products of the reaction of platinum tetrachloride with an olefin and a primary amine, a secondary amine, or both a primary amine and a secondary amine, such as the product of the reaction of platinum tetrachloride dissolved in 1-octene with sec-butylamine, or ammonium-platinum complexes as described in EP-B 110 370.

The platinum catalyst is preferably employed in amounts of from 0.05 mmol to 0.50 mmol, based on the amount of elemental platinum or the platinum compounds used per mole of the Si'H groups present in the siloxane employed. The reaction is preferably carried out at temperatures of from 0° C. to 110° C. and preferably at pressures of from 0.05 MPa to 1.0 MPa.

The hydrosilylation can be carried out in the presence or absence of solvents, such as hydrocarbons, ethers or esters. If the reaction is carried out in a solvent or solvent mixture, aprotic solvents or solvent mixtures having a boiling point of up to 160° C. at about 0.1 MPa are preferred. The individual reactants need not necessarily be soluble in the solvent, since the reaction can also be carried out in a suspension or emulsion. The reaction can also be carried out in a solvent mixture having a miscibility gap if at least one of the reactants is soluble in each of the two phases.

An advantage of this hydrosilylation process is that work-up of the reaction product containing organosilicon compounds (E) is not necessary before the elimination of the H—Z compounds in the second process step. After completion of the elimination reaction and purification of the organosilanes (P) formed as reaction product, these organosilanes (P) containing hydrolyzable radicals $R^2$ and preferably prepared from silanes of the general formula (5) can be equilibrated and condensed by known processes, as described, for example, in U.S. Pat. No. 5,214,077, to form organosiloxanes (P). In particular, the elimination process can also be used for the production of organosiloxanes (P) having a liquid-crystalline phase.

The organosilicon compounds (P) prepared by the elimination process can be used, for example, for the preparation of highly crosslinked coatings by polymerization, and if these compounds have liquid-crystalline phases, aligned and crosslinked layers having a liquid-crystalline structure can be produced and prepared for various applications. It is also possible to prepare compositions which comprise organosilicon compounds (P) which can be crosslinked to give polymers.

The elimination process enables the production of organosiloxanes and organosilanes (P) having a high concentration of α,β-unsaturated carboxylic acid radicals of high reactivity, such as, for example, acryloyl groups. In the polymerization of these compounds, a high crosslinking density is achieved. The coatings produced therefrom are particularly distinguished by increased hardness, improved scratch resistance and increased resistance to organic solvents.

The liquid-crystalline organosilanes and organosiloxanes (P) prepared by the elimination process can be used for the preparation of highly crosslinked, liquid-crystalline polymers, for which various possible applications are known from the prior art. Owing to their optically anisotropic properties, they are particularly suitable, for example, for the production of optically anisotropic layers, for example optical retardation films, interference pigments and wavelength- and polarization-selective optical filters.

The production of optically anisotropic layers of this type generally requires a uniform alignment of the mesogens in the shortest possible time after application of the layer. Such additional requirements, such as, for example, rapid alignment, which is favored by a low viscosity of the crosslinkable liquid-crystalline polymer, can be achieved more easily by admixing suitable low-molecular-weight components. The organosiloxanes (P) prepared by the elimination process are therefore also used in mixtures with other liquid-crystalline or non-liquid-crystalline materials so long as these additional mixture components do not prevent the formation of the liquid-crystalline phase.

The preferred additional mixture components used are compounds of the general formula (6) and compounds of the general formulae (9) and (10)

$$R^7-X^1-(A^1-X^2)_d-R^5-A^3 \qquad (9),$$

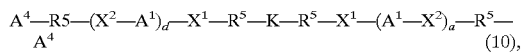

$$A^4-R^5-(X^2-A^1)_d-X^1-R^5-K-R^5-X^1-(A^1-X^2)_d-R^5-A^4 \qquad (10),$$

where $R^5$, $X^1$, $X^2$, $A^1$ and d, independently, can be the same or can be different from one another and are as defined for the general formulae (6) and (7), $R^7$ is selected from the group consisting of acryloyloxy, methacryloyloxy and acryloyl- and methacryloylethyleneoxy radicals and the group of radicals having the formula $H_2C=CH-(C_jH_{2j-1})$, in which j is an integer having a value of from 1 to 8, and in which one or more non-adjacent methylene units may be replaced by oxygen atoms or dimethylsilyl radicals, $A^3$ is selected from the group consisting of hydrogen atoms, halogen atoms, hydroxyl, nitrile, acryloyloxy, methacryloyloxy, acryl- and methacryloxyethyleneoxy radicals, cholestane radicals, cholesteryl radicals, doristeryl radicals, dianhydrohexitol radicals, cyclohexane radicals and alkenyl radicals having 1 to 10 carbon atoms, in which one or more non-adjacent methylene units may be replaced by oxygen atoms or dimethylsilyl radicals K is selected from the group consisting of dianhydrohexitol derivatives and in particular dianhydrosorbide or dianhydromannitol, $A^4$ are identical or different radicals selected from the group consisting of hydrogen atoms, halogen atoms, hydroxyl, nitrile, acryloyloxy, methacryloyloxy, acryl- and methacryloxyethyleneoxy radicals, cyclohexane radicals and alkenyl radicals having 1 to 10 carbon atoms, in which one or more non-adjacent methylene units may be replaced by oxygen atoms or dimethylsilyl radicals.

The invention likewise relates to optically anisotropic layers comprising liquid-crystalline organosiloxanes (P) prepared by the elimination process, or mixtures thereof, both with one another and with other liquid-crystalline or non-liquid-crystalline materials, so long as these additional mixture components do not prevent the formation of a liquid-crystalline phase.

The optically anisotropic layers are preferably produced by a process in which liquid-crystalline organosiloxanes (P) or mixtures containing organo-siloxanes (P) are applied to a substrate, aligned and subsequently fixed by a chemical reaction. The optically anisotropic layers are most preferably produced using liquid-crystalline organosiloxanes (P) prepared from compounds of the general formulae (4), (5), (6) and (7) and mixture components of the general formulae (6), (9) and (10).

The liquid-crystalline organosiloxanes (P) or an LC mixture containing the liquid-crystalline organosiloxanes (P) can be applied to the substrate surface in solution or as a dry substance at above the glass transition temperature of the solvent-free dry substance, for example by spin coating or using a knife coater or roller. If a solvent is used for the application, this must be removed in a subsequent drying step.

The thickness of the dry LC layer on the substrate depends on the requirements of the particular application. If the layer is used, for example, as a retardation plate, the necessary thickness is then the quotient of the optical retardation required and the optical anisotropy of the aligned LC layer. The thickness of the dry LC layer is preferably between 1 μm and 500 μm, particularly preferably between 1 μm and 60 μm, The application and alignment of the LC mixture can be carried out fully continuously, semi-continuously or discontinuously. A fully continuous process is described in U.S. Pat. No. 5,362,315.

The LC layer can be covered by a second substrate. The mesogens are aligned, for example, by shearing the material during application or, for example, after application through the interaction of the mesogens with the appropriately selected substrate surface(s) or by means of an electric field.

The LC mixture is preferably aligned in a temperature range from above the glass transition temperature to below the commencement of clearing of the particular LC mixture. In order to facilitate a simple industrial process, the composition of the LC mixture is preferably adjusted so that the suitable alignment temperature is between 20° C. and 150° C.

If the alignment of the mesogens is to take place through an interaction with the substrate surface(s), a suitable alignment layer can, in order to improve the aligning action, be applied to the substrate surface(s) by known coating, printing or dipping processes described in large number in the literature. The alignment layers or the substrates can be provided with a surface structure which favors alignment through additional treatment, for example rubbing. A local change in the alignment direction is possible, for example, by known methods for structuring the alignment layer by means of exposure to polarized UV light. Suitable methods for achieving a tilt between the mesogens of a liquid-crystalline phase and their interfaces are likewise described in the literature, for example the vapor deposition of inorganic materials at an oblique angle. In order to achieve a tilt of the mesogens at an angle of from 10° to 80° relative to the substrate surface, a layer of silicon oxide is particularly preferably applied by vapor deposition.

Substrates which can be used are all materials which are known for the production of optical elements. Preference is given to organic and inorganic substrates which are transparent or semi-transparent in the wavelength range relevant for the particular application. The substrates can be planar or curved. Particular preference is given to substrates which do not change their physical properties at the production, processing and use temperature of the LC layers.

Very particular preference is given to glass and quartz plates and polymer films, such as, for example, polycarbonates, polysulfones, polyethylene terephthalates, polyimides and cellulose acetates. If necessary, the substrate (s) can be provided with an additional alignment aid, such as, for example, a layer of polyimide, polyamide, polyvinyl alcohol or silicon oxide.

When the alignment is complete, the liquid-crystalline organosiloxanes (P) or the LC mixtures containing these liquid-crystalline organosiloxanes (P) are fixed in the optically anisotropic layers. To this end, the organosiloxanes (P) are crosslinked via the $\alpha,\beta$-unsaturated carboxylic acid radicals present in the mesogenic radicals. This crosslinking is preferably effected by means of free radicals generated by peroxides or other suitable thermally activatable free-radical formers, by UV light, by high-energy electromagnetic radiation, or by warming. However, the crosslinking can also be effected by means of crosslinking agents containing hydrogen atoms bonded directly to silicon with catalysis by platinum metal catalysts. It can also take place cationically or anionically. Particular preference is given to the UV light crosslinking described in U.S. Pat. No. 5,211,877 and U.S. Pat. No. 5,214,077.

The resultant fixed layer can be used together with the substrate in the form of a laminate, as a film open on one side, or, after removal of the substrate(s), also as a free film. Preference is given to the use as a film together with the substrate or as a film open on one side.

Another use form of the optically anisotropic layers is as optically anisotropic platelets, which are also referred to hereinbelow as LC platelets. U.S. Pat. No. 5,362,315 discloses how pigments having a liquid-crystalline structure with a chiral phase which reflect light in colors can be prepared by detaching a polymerized cholesteric film from the substrate and subsequently comminuting the rough fragments obtained in this way. The pigments can then be incorporated into a suitable binder system and applied to a substrate. DE-A-196 19 460 describes how platelets having a negative refractive index anisotropy for visible light can be prepared and used by a similar process. The layers described above can likewise be comminuted after crosslinking to give optically anisotropic platelets and subsequently incorporated into a binder and applied to a substrate.

The LC platelets are most preferably produced using liquid-crystalline organosiloxanes and organosilanes (P) prepared by the elimination process from compounds of the general formulae (4), (5), (6) and (7) and mixture components of the general formulae (6), (9) and (10).

Coherent films of the layers of liquid-crystalline organosiloxanes (P) can be employed for all purposes for which the optically anisotropic layers of positive and negative refractive index anisotropy are suitable, for example as optical retarder films for improving the properties of liquid-crystal displays, which are described in large number in the literature. Depending on the choice of substrates and alignment layers and the composition of the liquid-crystalline organosiloxanes (P) and the LC mixtures containing these organosiloxanes (P), it is possible to achieve different forms of alignment, which can advantageously be employed, for example, in liquid-crystal displays, such as TN or STN displays. Examples of possible alignments of the mesogens in the layers are a homogeneous and planar alignment of all mesogens, a hybrid alignment in which the alignment changes continuously from planar to homeotropic from one surface to the opposite surface, a completely homeotropic alignment of all mesogens, a planar alignment which is twisted about the surface perpendiculars, in which the mesogens are aligned, for example, by doping with a chiralic or by means of mutually twisted alignment layers, in a similar manner to in a TN or STN cell, or a cholesteric alignment with a pitch which is less than the wavelength of visible light, which, as described in DE-A-196 19 460, results in a negative refractive index anisotropy.

Further applications can be accomplished through slight modification of the above-described process for the production of the optically anisotropic layers. For example, absorptive polarizing filters can be produced if a mixture is used which, in addition to the liquid-crystalline organosiloxanes (P), also contains suitable dye molecules which align along the mesogens and at the same time do not prevent the formation of the liquid-crystalline phase. Optical storage media, which are based on a local change in the refractive index, can be produced by locally modifying the alignment of the mesogenic radicals of the liquid-crystalline organosiloxane (P) before crosslinking. This can be achieved, for example, by local UV crosslinking through a mask which is opaque to UV radiation if the alignment forces acting from the outside or the temperature of the LC layer are modified between the individual exposure steps. Another possibility is structuring of the alignment layer, as used, for example, in LCD manufacture for the production of sub-pixels.

If the liquid-crystalline organosiloxanes (P) or mixtures thereof either with one another or with other liquid-crystalline or non-liquid-crystalline which do not prevent the formation of a liquid-crystalline phase, contain compounds which induce a chiral nematic phase (chiralics), then these can be used for the production of polarizing and wavelength-selective optical filters or LC platelets.

Cholesteric liquid crystals (CLCs) of this type reflect circular-polarized electromagnetic radiation in a wavelength range which depends on the helical structure of the CLC. The chiralics produce either a right-handed or left-handed twisted structure which reflects circular-polarized light of the same helicity. The central wavelength of the reflection band, which is referred to below as the reflection wavelength, is determined by the refractive index and the pitch of the helical structure, which decreases with increasing concentration of the chiralic. In addition, the reflection wavelength is dependent on the viewing angle.

The width of the band is determined by the optical anisotropy of the mesogenic radicals of the liquid-crystalline organosiloxanes (P) and the other mixture components. In most cases, it is between 5% and 15% of the reflection wavelength. For special applications, suitable measures during film production, as described, for example, in U.S. Pat. No. 5,506,704 and U.S. Pat. No. 5,691,789, allow a varying pitch of the helical structure to be produced, which results in an additionally broadened reflection band.

A large number of suitable optically active dopants are known from the literature. For materials with a left-handed helix, it is often possible to rely on cholesterol compounds, which, in addition to chirality, also introduce good mesogenic properties, for example the cholesterol derivatives disclosed by H. Finkelmann, H. Ringsdorf et al., in Makromol. Chem. 179, 829–832 (1978). A suitable steroid system with a right-handed helix based on cholest-8(14)-en-3-ol (doristerol) or derivatives thereof is described in U.S. Pat. No. 5,695,680. Non-steroidal systems tend to reduce the stability of the liquid-crystalline phase at high concentrations. Examples are the tartarimide derivatives disclosed in U.S. Pat. No. 4,996,330 and U.S. Pat. No. 5,502,206. DE-A-43 42 280 and DE-A-44 08 171 describe crosslinkable monomeric hexitol derivatives and mixtures of monomeric dianhydrohexitol derivatives with other liquid-crystalline compounds which are employed as monomeric dopants for the production of cholesteric networks. DE-A-196 19 460 claims liquid-crystal mixtures which contain liquid-crystalline organosiloxanes and dianhydrohexitol derivatives as chiral additives with a left-handed or right-handed helix. The dianhydrohexitol derivatives described therein are preferably compounds from the group consisting of dianhydrosorbide, dianhydromannitol and dianhydroiditol.

CLC mixtures of this type which contain liquid-crystalline organosiloxanes (P) and chiralics can be used for the production, by the process described above, of layers having a cholesteric alignment which reflect circular-polarized light wavelength-selectively. In these applications, the thickness of the LC layer is preferably greater than three times the pitch, up to a maximum layer thickness of 500 $\mu$m. Layer thicknesses of from 1 $\mu$m to 50 $\mu$m are particularly preferred.

Layers of this type having a cholesteric alignment are highly suitable for decorative applications if the concentration of the chiralics is selected so that the reflection wavelength of the cholesteric band is in the visible wavelength region. Owing to the viewing angle-dependent color impression and the metallic sheen, these layers facilitate special color effects. In applications in security paper printing and trademark protection, good copying protection is additionally achieved owing to these color effects and the polarization of the reflected light.

An example of an optical application is a planar CLC filter, as described in U.S. Pat. No. 859,03 1. CLC filters which reflect in the infra-red region (IR) can be employed, for example, for heat-protection glazing. U.S. Pat. No 5,682,212 discloses how wavelength- and polarization-selective elements which are optically imaging for visible light as far as the near ultra-violet (UV) can be produced on curved substrates using cholesteric liquid crystals. Possible use forms of these optical elements are, for example, beam splitters, mirrors and lenses. The liquid-crystalline organosiloxanes (P) are suitable for the production of optical elements of this type from the IR into the UV region, which is accessible, for example, by using the mixtures described in DE-A-196 19 460.

In some applications of the optically anisotropic layers, it is also possible to use a layer containing LC platelets instead of a coherent film. In this way, the special optical effects of the liquid-crystalline organosiloxanes (P) can be applied with significantly less effort, since the user can utilize conventional printing and coating technologies instead of himself carrying out the more complex production of the films, which requires an alignment and crosslinking operation.

To this end, the LC platelets are incorporated into a suitable binder system, as described, for example, in U.S. Pat. No. 5,362,315 and U.S. Pat. No. 5,683,622. The LC platelets containing liquid-crystalline organosiloxanes (P) containing $\alpha,\beta$-unsaturated carboxylic acid radicals of high reactivity, such as, for example, acryloyl groups, are particularly suitable for this purpose since, owing to their high crosslinking density, they have improved stability in the binder.

The requisite properties of the binder systems, in particular the optical properties, also depend on the intended application of the LC platelets. For example, in applications which utilize the polarization- and wavelength-selective reflection of LC platelets containing chiral additives, the binders preferably employed are optically transparent at least in the region of the reflection wavelength. For applications which utilize the optical anisotropy in the region of visible light, preferred binders are colorless and transparent throughout the visible wavelength region.

Preferred binder systems for optical elements are those whose mean refractive index after curing is similar to the mean refractive index of the LC platelets. For the production of durable layers containing LC platelets, curable binder systems are preferably suitable. However, non-curable binders, such as, for example, oils, pastes or thermoplastics, can also be used for specific applications.

Particular preference is given to binder systems which do not alter the physical properties of the LC platelets, or only do so in a defined manner. Examples of suitable binder systems are polymerizable resins (UP resins, silicone resins, epoxy resins), dispersions, solvent-containing or water-based coatings, or all transparent plastics, for example polyvinyl chloride, polymethyl methacrylate and polycarbonate. Besides these isotropic binders, the binder used can also be liquid-crystalline systems, for example liquid-crystalline polymers or polymerizable liquid-crystalline resins, and polymerizable LC silicones. In order to produce a layer or a film having specific optical properties, the LC platelets are stirred into a liquid binder. The alignment of the platelets parallel to the surface of the layer is achieved, as in surface coating with liquid-crystalline colored pigments, for example as described in U.S. Pat. No. 5,362,315, on application of a thin layer of the pigment/binder mixture to a substrate or on extrusion of the mixture. Depending on the requirements of the particular application and the properties of the binder, the film can be detached from the substrate after curing.

The applications of the LC platelets produced can, as in the case of the films, be restricted to pure phase retardation of electromagnetic waves from the ultra-violet to the infra-red region or, if a liquid-crystalline organosiloxane containing chiralics is used for the production of the platelets, LC platelets having a liquid-crystalline structure with a chiral phase which reflect electromagnetic waves of a certain wavelength in a circular-polarized manner can also be produced therefrom, as described in U.S. Pat. No. 5,362,315.

An example of an application of LC platelets is the production of optically imaging, wavelength- and polarization-selective elements on curved substrates, as described in U.S. Pat. No. 5,683,622.

The LC platelets are particularly suitable for decorative purposes if the concentration of the chiralics is selected so that the reflection wavelength of the cholesteric band is in the visible wavelength region. In applications in security paper printing and trademark protection, the viewing angle-dependent color impression and the polarization of the reflected light are additional security features. On simultaneous use of LC platelets having a left-handed and right-handed helical structure, prints can be produced, as described in U.S. Pat. No. 5,599,412, which allow the formation of a three-dimensional image on viewing through polarizing spectacles.

For the production of security marks for protection against counterfeiting of, for example, bank notes, security paper prints, documents or in trademark protection, LC platelets can be employed with particular advantage since they can usually be incorporated with relatively little effort into the printing or other coating processes which already exist in these applications. As marks which are invisible to the human eye, IR-reflective LC platelets, which are obtained at low concentrations of chiralics, or UV-reflective LC platelets, which are obtained at high concentrations of chiralics, are particularly suitable since, owing to their good reflection, they can easily be read by instruments having suitable detectors. For such applications, the LC platelets are preferably transparent and colorless in the region of visible light. The wavelength of the reflection band here is preferably above 750 nm or below 400 nm. Besides the reflection wavelength, the circular polarization of the reflected radiation can be detected as an additional security feature. For this application, the CLC platelets are preferably incorporated into an IR- or UV-transparent binder for application to a substrate to be marked.

In the examples below, all amounts and percentages are by weight, all pressures are 0.10 MPa (abs.) and all temperatures are 20° C., unless stated otherwise.

Example 1 a) 58.08 g (1.0 mol) of allyl alcohol were dissolved in 200 ml of toluene, and 190.46 g (1.5 mol) of 3-chloropropionyl chloride were added dropwise at 90° C. The reaction solution was refluxed for a further 1.5 hours. The organic phase was washed with 10% strength NaOH solution and twice with $H_2O$, and the solvent was evaporated. The product was subsequently distilled at 74° C. and 20 mbar, giving 104.3 g of allyl 3-chloropropionate (71% of theory).

b) 37.15 g (0.25 mol) of allyl 3-chloropropionate and 15.48 g (0.052 mol) of pentamethylpentacyclosiloxane were dissolved in 200 ml of toluene, and 0.94 ml of a 1% strength hexachloroplatinic acid solution was added at 80° C. The reaction solution was stirred at 80° C. for 1 hour and subsequently reacted with 75.9 g (0.75 mol) of triethylamine and 0.09 g of 2,6-di-tert-butyl-4-(dimethylaminomethylene) phenol (Ethanox® 703, Ethyl Corp., Baton Rouge, La. 70801). After the mixture had been stirred at 80° C. for 8 hours, the triethylammonium chloride precipitate was filtered off, and the solution was dried to a residual solvent content of less than 0.5%, giving 39.2 g of an organosiloxane having a content of 10% of higher oligomers.

Example 2 a) 77.8 g (0.47 mol) of eugenol (2-methoxy-4-(2'-propenyl)phenol) were dissolved in 100 ml of toluene, and 90.3 g (0.71 mol) of 3-chloropropionyl chloride were added dropwise at 90° C. The reaction solution was refluxed for a further 1.5 hours. The organic phase was washed with 10% strength NaOH solution and twice with $H_2O$, and the solvent was evaporated. The product was subsequently distilled at 135° C. and 40 mbar, giving 92.9 g of 2-methoxy-4-(2'-propenyl)phenyl 3"-chloropropionate (77% of theory).

b) 19.87 g (0.078 mol) of 2-methoxy-4-(2'-propenyl) phenyl 3"-chloropropionate and 6.50 g (0.010 mol of Si—H) of a linear organosiloxane having a mean chain length of eight were dissolved in 150 ml of toluene and 0.75 ml of a 1% strength hexachloroplatinic acid solution was added at 80° C. The reaction solution was stirred at 80° C for 1 hour, and 11.4 g (0.117 mol) of triethylamine and 0.05 g of 2,6-di-tert-butyl-4-(dimethylaminomethylene)phenol (Ethanox® 703) were subsequently added. After 2 hours at 80° C., the triethylammonium chloride precipitate was filtered off, and the solution was dried to a residual solvent content of less than 0.5%, giving 24.0 g of an organosiloxane having a mean molecular weight of 3500 and a distribution of 1.4 ($M_w/M_n$).

Further organosiloxanes and organosilanes containing acryloyl groups were prepared analogously to Examples 1 and 2. The contents of higher oligomers measured by GPC after these syntheses and the molecular weight distributions $M_{w/Mn}$ for linear organosiloxanes having a mean chain length of n=8 and the viscosities of the reaction products are shown in the table below:

| Reaction | Proportion of higher oligomers or $M_w/M_n$ | Viscosity of the reaction product |
|---|---|---|
| Dimethylchlorosilane/ allyl 3-chloropropionate | 15% | 0.01 Pas at 25° C. 9.4 cSt at 25° C. |
| Dimethylchlorosilane/2-methoxy-4-(2'-propenyl) phenyl 3"-chloropropionate | 5% | 0.09 Pas at 25° C. 85 cSt at 25° C. |
| Triethoxysilane/allyl 3-chloropropionate | 20% | 0.005 Pas at 25° C. 3.1 cSt at 25° C. |
| Triethoxysilane/2-methoxy-4-(2'-propenyl)-phenyl 3"-chloropropionate | 13% | 0.37 Pas at 25° C. 341 cSt at 25° C. |
| Pentamethylcyclopenta-siloxane/allyl 3-chloropropionate | 10% | 0.1 Pas at 50° C. |
| Pentamethylcyclopenta-siloxane/2-methoxy-4-(2'-propenyl)phenyl 3"-chloropropionate | 20% | 0.5 Pas at 90° C. |
| Organosiloxane (n = 8)/ allyl 3-chloropropionate | 1.7 ($M_wM_n$) | 0.2 Pas at 30° C. |
| Organosiloxane (n = 8)/ 2-methoxy-4-(2'-propenyl) phenyl 3"-chloropropionate | 1.4 ($M_w/M_n$) | 0.5 Pas at 90° C. |

Example 3 a) 228.5 g (1.8 mol) of 3-chloropropionyl chloride were added dropwise at 115° C. to a solution of 324.4 g (1.2 mol) of 4'-hydroxyphenyl 4-allyloxybenzoate (prepared as described in U.S. Pat. No. 5,211,877) in 500 ml of o-xylene. When the addition of the 3-chloropropionyl chloride was complete, the reaction solution was stirred for a further 3 hours. The solution was cooled to 90°, and the excess acid chloride was washed out using 30 g of NaOH as a 5% strength aqueous solution. The residual water was removed, the mixture was diluted with 750 ml of petroleum ether, and the product was crystallized out by cooling. The 1-(4'-allyloxybenzoyloxy)-4-(4"-(3'"-chloropropionyloxy)) benzene was filtered off, washed with petroleum ether and dried, giving 363.4 g (84% of theory) of 1-(4'-allyloxybenzoyloxy)-4-(4"-(3'"-chloropropionyloxy)) benzene having a melting point of 119° C.

b) 308.6 g (1.8 mol) of 3-bromopropionyl chloride were added dropwise at 115° C. to a solution of 324.4 g (1.2 mol) of 4'-hydroxyphenyl 4-allyloxybenzoate (prepared as described in U.S. Pat. No. 5,211,877) in 500 ml of o-xylene. When the addition of the 3-bromopropionyl chloride was complete, the reaction solution was stirred for a further 3 hours. The solution was cooled to 90°, and the excess acid chloride was washed out using 30 g of NaOH as a 5% strength aqueous solution. The residual water was removed, the mixture was diluted with 750 ml of petroleum ether, and the product was crystallized out by cooling. The 1-(4'-allyloxybenzoyloxy)-4-(4"-(3'"-bromopropionyloxy)) benzene was filtered off, washed with petroleum ether and dried, giving 418.5 g (86% of theory) of 1-(4'-allyloxybenzoyloxy)-4-(4"-(3'"-bromopropionyloxy))benzene having a melting point of 122° C.

Example 4

73.8 g (0.2 mol) of 1-(4'-allyloxybenzoyloxy)-4-(4"-(3'"-bromopropionyloxy))benzene from Example 3 were dissolved in 500 ml of toluene, the mixture was warmed to 80° C., and 0.66 g of 2,6-di-tert-butyl-4-(dimethylaminomethylene)phenol (Ethanox® 703) was added. 22.2 g (0.22 mol) of triethylamine were added dropwise, and the solution was stirred at 80° C. for 1 hour. Excess triethylamine and triethylammonium hydrochloride were washed out using dilute sulfuric acid and water, and the reaction solution was then dried azeotropically. The product was precipitated by addition of 500 ml of petroleum ether and was recrystallized from isopropanol, giving 61.6 g (95% of theory) of 1-(4'-allyloxybenzoyloxy)-4-(4"-acryloyloxy)benzene having a nematic phase between a melting point of 94° C. and a clearing point of 108° C.

Example 5 a) 30.05 g (0.083 mol) of 1-(4'-allyloxybenzoyloxy)-4-(4"-(3'"-chloropropionyloxy))benzene and 5.41 g (0.018 mol) of pentamethylcyclopentasiloxane were dissolved in 110 ml of toluene, and 0.67 ml of a 1% strength hexachloroplatinic acid solution was added at 80° C. When the exothermic evolution of heat had subsided, the solution was stirred at 90° C. for 90 minutes and then cooled to 80° C., 9.65 g (0.096 mol) of triethylamine and 0.09 g of 2,6-di-tert-butyl-4-(dimethylaminomethylene)phenol (Ethanox® 703) were added, and the mixture was stirred at 80° C. for 1.5 hours. The reaction mixture was cooled to 20° C., insoluble triethylammonium hydrochloride was filtered off, and the crude product was precipitated using petroleum ether/ethanol (2:1). The precipitate was dissolved in toluene, and the solution was filtered and dried to a residual solvent content of less than 0.5%, giving 29.9 g (79% of theory) of an organosiloxane having a nematic phase between a glass transition temperature of 21° C. and a clearing point of 117° C.

b) 32.44 g (0.08 mol) of 1-(4'-allyloxybenzoyloxy)-4-(4"-(3'"-bromopropionyloxy))benzene and 5.41 g (0.018 mol) of pentamethylcyclopentasiloxane were dissolved in 110 ml of toluene, and 0.67 ml of a 1% strength hexachloroplatinic acid solution was added at 80° C. When the exothermic evolution of heat had subsided, the solution was stirred at 90° C. for 90 minutes and then cooled to 30° C., 9.26 g (0.092 mol) of triethylamine and 0.11 g of 2,6-di-tert-butyl4-(dimethylaminomethylene)phenol (Ethanox® 703) were added, and the mixture was stirred at 80° C. for 3 hours. The reaction mixture was cooled to 20° C., insoluble triethylammonium hydrochloride was filtered off, and the crude product was precipitated using petroleum ether/ethanol (2:1). The precipitate was dissolved in toluene, and the solution was filtered and dried to a residual solvent content of less than 0.5%, giving 33.93 g (81% of theory) of an organosiloxane having a nematic phase between a glass transition temperature of 23° C. and a clearing point of 116° C.

Example 6

42.07 g (0.116 mol) of 1-(4'-allyloxybenzoyloxy)-4-(4"-(3'"-chloropropionyloxy))benzene and 7.57 g (0.032 mol) of tetramethyltetracyclosiloxane were dissolved in 150 ml of toluene, and 0.94 ml of a 1% strength hexachloroplatinic acid solution was added at 80° C. When the exothermic evolution of heat had subsided, the solution was stirred at 90° C. for 90 minutes and then cooled to 80° C., 13.51 g (0.134 mol) of triethylamine and 0.13 g of 2,6-di-tert-butyl-4-(dimethylaminomethylene)phenol (Ethanox® 703) were added, and the mixture was stirred at 80° C. for 1.5 hours. The reaction mixture was cooled to 20° C., insoluble triethylammonium hydrochloride was filtered off, and the crude product was precipitated using petroleum ether/ethanol (2:1). The precipitate was dissolved in toluene, and the solution was filtered and dried to a residual solvent content of less than 0.5%, giving 40 g (75% of theory) of an organosiloxane having a nematic phase between a glass transition temperature of 17° C. and a clearing point of 111° C.

Example 7

28.65 g (0.079 mol) of 1-(4'-allyloxybenzoyloxy)-4-(4"-(3'"-chloropropionyloxy))benzene and 6.72 g (0.0105 mol) of H-siloxane (mean chain length n=8) were dissolved in 100 ml of toluene, and 0.60 ml of a 1% strength hexachloroplatinic acid solution was added at 80° C. When the exothermic evolution of heat had subsided, the solution was stirred at 90° C. for 90 minutes and then cooled to 80° C, 10.04 g (0.099 mol) of triethylamine and 0.07 g of 2,6-di-tert-butyl-4-(dimethylaminomethylene)phenol (Ethanox® 703) were added, and the mixture was stirred at 80° C. for 1.5 hours. The reaction mixture was cooled to 20° C., insoluble triethylammonium hydrochloride was filtered off, and the solution was dried to a residual solvent content of less than 0.5%, giving 30.3 g of an organosiloxane having a nematic phase between a glass transition temperature of 10° C. and a clearing point of 66° C.

Example 8 a) 37.53 g(0.22 mol) of 4-methoxybenzoyl chloride were added dropwise at 145° C. over the course of 1 hour to a solution of 54.06 g (0.2 mol) of 4'-hydroxyphenyl 4-allyloxybenzoate (prepared as described in U.S. Pat. No. 5,211,877) in 250 ml of o-xylene. When the addition of the acid chloride was complete, the reaction solution was stirred for a further 3 hours. The solution was cooled to 95° C. and washed with 10% strength NaOH solution and $H_2O$ until neutral. Excess water was removed azeotropically, and the product was crystallized out by cooling and filtered off, giving 55.8 g of 1-(4'-allyloxybenzoyloxy)-4-(4"-(4'"-methoxy-benzoyloxy))benzene (69% of theory) having a melting point of 161° C.

108.26 g (0.30 mol) of 1-(4'-allyloxybenzoyloxy)-4-(4"-(3'"-chloropropionyloxy))benzene, 33.3 g (0.075 mol) of 1-(4'-allyloxybenzoyloxy)-4-(4"-(4'"-methoxybenzoyloxy))benzene and 24.35 g (0.081 mol) of pentamethylcyclopentasiloxane were dissolved in 100 ml of toluene, and 1.4 ml of a 1% strength hexachloroplatinic acid solution were added at 80° C. When the exothermic evolution of heat had subsided, the solution was stirred at 90° C. for 90 minutes and then cooled to 80° C., 37.95 g (0.375 mol) of triethylamine and 0.3 g of 2,6-di-tert-butyl-4-(dimethylaminomethylene)phenol (Ethanox® 703) were added, and the mixture was stirred at 80° C. for 1.5 hours. The reaction mixture was cooled to 20° C., insoluble triethylammonium hydrochloride was filtered off, and the solution was dried to a residual solvent content of less than 0.5%, giving 147.4 g of an organosiloxane having a nematic phase between a glass transition temperature of 21° C. and a clearing point of 151° C.

Example 9 a) 276.6 g of 4-chlorobutyl acetate (1.8 mol) were added to a solution of 249 g of ethyl 4-hydroxybenzoate (1.5 mol), 3 g of potassium iodide (0.018 mol) and 248 g of potassium carbonate (1.8 mol) in 2 l of DMF, and the mixture was stirred at 90° C. for 11 hours. The reaction mixture was poured into 5 l of ice-water, and the precipitate was filtered off with suction and washed with 4 l of ice-water. The crude product was dissolved in 3 l of ethanol, potassium hydroxide (400 g) was added, and the mixture was refluxed for 3 hours. The reaction mixture was poured into 6 l of ice-water and acidified using concentrated hydrochloric acid, and the precipitate was filtered off. The precipitate was washed with water until neutral and subsequently dried, giving 282.1 g of 4-(4'-hydroxybutoxy)benzoic acid (yield 89%).

A solution of 282 g of 4-(4'-hydroxybutoxy)benzoic acid (1.34 mol), 325 ml of freshly distilled methacrylic acid (3.35 mol), 0.3 g of 2,6 di-tert-butyl-4-(dimethylaminomethylene) phenol (Ethanox® 703) and 23.7 g of p-toluenesulfonic acid in 1.1 l of 1,1,1-trichloroethane was refluxed for 10 hours on a water separator. The reaction mixture was cooled to 60° C.–70° C. and stirred into 2.5 l of petroleum ether, and the precipitate was filtered off. After washing with petroleum ether, the precipitate was dried under reduced pressure at room temperature for 24 hours, giving 223.7 g of 4-(4'-methacryloxybutoxy)benzoic acid (yield 60%).

4.8 g of thionyl chloride (0.04 mol) were added at 80° C. to 10 g of 4-(4'-methacryloxybutoxy)benzoic acid (0.036 mol) and 0.01 g of 2,6-di-tert-butyl-4-(dimethylaminomethylene)phenol (Ethanox® 703) in toluene (40 ml), and the mixture was stirred for 30 minutes until the evolution of gas had subsided. The excess thionyl chloride was removed by distillation, and the product was subsequently added at 0° C. to 5 ml of pyridine and 5 ml of toluene and extracted twice with 100 ml of dichloromethane each time. After the combined organic extracts had been dried over calcium chloride, 50 mg of hydroquinone were added, and the mixture was evaporated. The residue was chromatographed on silica gel (toluene/ethyl acetate (5:1)), giving 7.5 g of bis-1,4-[4'-(4"-methacryloxybutoxy) benzoyloxy]benzene (yield 66%) having a nematic phase between a glass transition temperature of 89° C. and a clearing point of 146° C.

Example 10 a) 902.6 g of 2-acetylisosorbide (4.8 mol) as described in EP 057 847 were dissolved in 1.7 l of xylene, and a solution of 900 g of anisoyl chloride (5.3 mol) in 200 ml of xylene was added. The mixture was refluxed for 5 hours. When the reaction was complete, the mixture was cooled to room temperature, during which the product precipitated. The crystal cake was filtered off with suction, washed with 600 ml of petroleum ether and dried in air, giving 1278.8 g of 2-acetyl-5-anisoylisosorbide (yield 83%).

b) 639 g of 2-acetyl-5-anisoylisosorbide (1.98 mol) were introduced into 2.5 l of methanol, and 269.4 ml of 25% strength aqueous ammonia solution (3.96 mol) were added. The solution was stirred at 55° C. for 3 hours. The solvent and the excess ammonia were evaporated under reduced pressure, and the residue was dried under reduced pressure. The reaction of 5-anisoylisosorbide was carried out without further purification.

c) 232.35 g (0.83 mol) of the resultant 5-anisoylisosorbide, 230.0 g (0.87 mol) of 4-(4'-acryloylbutoxy)benzoic acid (prepared analogously to Example 9b using acrylic acid instead of methacrylic acid), 30 mg of 2,6-di-t-butyl-4-(dimethylaminomethylene)phenol (Ethanox® 703) and 5.5 g of dimethylaminopyridine were dissolved in 1 l of methylene chloride, and the solution was cooled to 6° C. 196.7 g (0.95 mol) of DCC were added at this temperature, and the mixture was stirred for 1 hour and subsequently warmed to room temperature. Precipitated dicyclohexylurea was filtered off, the solvent was stripped off under reduced pressure, and the residue was recrystallized from 1.5 ml of isopropanol. The crystals were washed again with 1 l of isopropanol, giving 357 g of 2-[4'-(4'-acryloylbutoxy)benzoyl]-5-anisoylisosorbide (yield 82%) having a melting point of 82° C.

Example 11 a) 18 g (0.06 mol) of 4-(4'-(3"-chloropropionyloyl) butoxy)benzoic acid (prepared analogously to Example 9b using 3-chloropropionic acid instead of methacrylic acid) were dissolved in 20 ml of toluene, 5.85 g (0.081 mol) of thionyl chloride were added, and the mixture was refluxed for 3 hours. The excess thionyl chloride was then evaporated off under reduced pressure together with 50% of the solvent. The remaining solution was added dropwise to a solution of 15 g (0.049 mol) of 5-(4'-allyloxybenzoyl)isosorbide (prepared analogously to Example 10a,b using 4-allyloxybenzoyl chloride instead of anisoyl chloride in step 10a) in 1 l of toluene. The mixture was heated at the boil for 21 hours. For work-up, the batch was washed twice with both saturated NaHCO$_3$ and NaCl solution, and the solvent was evaporated off under reduced pressure. Any 4-(4'-(3"-chloropropionyloxy)butoxy)benzoic acid still present was separated off by passing the mixture through a filter column over silica gel with ethyl acetate/petroleum ether in a solvent ratio of 1:2. The product was then recrystallized from isopropanol, giving 11.6 g (40% of theory) of 5-(4'-allyloxybenzoyl)-(4"-(4'"-(3""-chloropropionyl)oyl)-butoxybenzoyl)isosorbide having a melting point of 55° C.

b) 20.0 g (0.074 mol) of 4'-hydroxyphenyl 4-allyloxybenzoate (prepared as described in U.S. Pat. No. 5,211,877) were dissolved in 100 ml of toluene at 95° C., and 35.4 g (0.11 mol) of 4-(3'-chloropropionyloxybutoxy) benzoyl chloride (as a solution from 11a) were added dropwise at 90° C.–100° C. The reaction solution was stirred for a further 5 hours, and the product was precipitated by addition of 200 ml of petroleum ether and cooling to 20° C. and was filtered off. The product was re-dissolved in ethyl acetate, neutralized using 5% strength NaOH solution, washed and crystallized out by evaporation, giving 19.8 g (49% of theory) of 4'-(4"-(3'"-chloro-propionyloyl)butoxy) benzoyl)phenyl 4-allyloxybenzoate having a melting point of 95° C.

c) 13.5 g (0.024 mol) of 4'-(4"(3'"-chloro-propionyloyl) butoxy)benzoyl)phenyl 4-allyloxybenzoate, 3.44 g (0.006 mol) of 5-(4'-allyloxybenzoyl)-(4"-(4'"-(3""-chloropropionyloyl)butoxy)benzoyl)isosorbide and 2.6 g (0.011 mol) of tetramethyltetracyclosiloxane were dissolved in 90 ml of toluene, and 0.8 g of a 0.5% strength hexachloroplatinic acid solution was added at 70° C. The reaction solution was stirred at 80° C. for a further 1.5 hours. 9.1 g (0.09 mol) of triethylamine and 0.02 g of 2,6-di-tert-butyl-4-(dimethylamino-methylene)phenol (Ethanox® 703) were subsequently added to the solution, and the mixture was stirred at 80° C. for a further 8 hours. The reaction mixture was cooled to room temperature, the precipitated triethylammonium chloride was filtered off, and the product was precipitated by addition of 250 ml of ethanol at 0° C. and dried to a residual solvent content of less than 0.5%, giving 8.3 g of an organosiloxane having a cholesteric phase between a glass transition temperature of 28° C. and a clearing point of 83° C.

d) 2 g of the organosiloxane and 0.01 g of the photoinitiator 2-methyl-1-[4-(methylthio)phenyl]-2-morpholino-1- propanone (Irgacure® 907 from Ciba-Geigy AG) were dissolved in 30 ml of para-xylene, and the solution was filtered through a 0.45 µm membrane filter and freeze-dried. Two glass plates were each provided with an alignment layer of polyvinyl alcohol, which was rubbed unidirectionally with a velvet cloth. 0.1 g of the dried mixture was applied to the alignment layer of one of the glass plates at 90° C. and covered with the second plate in such a way that the rubbing directions were opposite and parallel. The mixture was distributed by uniform pressure on the plates until a film with a thickness of approximately 10 µm remained between the alignment layers. The film was conditioned at 75° C. for 5 minutes until a uniform alignment had been achieved and was subsequently polymerized by irradiation with UV-A light (about 100 mW/cm$^2$ for 15 seconds). The crosslinked film exhibited a blue color when viewed perpendicularly, which changed to the violet region with increasing viewing angle.

Example 12

5 g of the organosiloxane from Example 5a, 2.1 g of 1-(4'-allyloxybenzoyloxy)-4-(4"-acryloyloxy)benzene from Example 4 and 0.035 g of Irgacure® 907 were dissolved in 75 ml of para-xylene, and the solution was filtered through a 0.45 µm membrane filter and freeze-dried. The mixture had a glass transition temperature of 7° C. and a clearing point of 106° C.

Two glass plates were each provided with an alignment layer of polyvinyl alcohol, which was rubbed unidirectionally with a velvet cloth. 0.1 g of the mixture was applied to the alignment layer of one of the glass plates at 90° C. and covered with the second plate in such a way that the rubbing directions were opposite and parallel. The mixture was distributed by uniform pressure on the plates until a film with a thickness of approximately 7 µm remained between the alignment layers. The film was conditioned at 90° C. for 10 minutes until a monodomain having a homogeneous planar alignment had been achieved and all disclination lines had disappeared. It was subsequently polymerized by irradiation with UV-A light (about 100 mW/cm$^2$ for 15 seconds). The resultant colorless and clear film exhibited an optical path difference of 910 nm at a light wavelength of 633 nm using the Sénarmont method.

Example 13

6 g of the organosiloxane from Example 6, 1.5 g of 1-(4'-allyloxybenzoyloxy)-4-(4"-acryloyloxy)benzene from Example 4 and 0.035 g of Irgacure® 907 were dissolved in 75 ml of para-xylene, and the solution was filtered through a 0.45 µm membrane filter and freeze-dried. The mixture had a glass transition temperature of 17° C. and a clearing point of 111° C.

As in Example 12, this mixture was used to produce an aligned and crosslinked film with a thickness of about 12 µm between glass plates with the alignment layers. The colorless and clear film exhibited an optical path difference of 640 nm at a wavelength of 633 nm using the Sénarmont method.

Example 14

7 g of the organosiloxane from Example 8b, 2 g of bis-1,4-[4'-(4"-methacryloxybutoxy)benzoyloxy]benzene from Example 9c and 0.045 g of Irgacure® 907 were dissolved in 100 ml of para-xylene, and the solution was filtered through a 0.45 µm membrane filter and freeze-dried. As in Example 12, this mixture was used to produce an aligned and crosslinked film with a thickness of about 11 µm between glass plates with the alignment layers. The colorless and clear film exhibited an optical path difference of 1270 nm at a wavelength of 633 nm using the Sénarmont method.

Example 15

85.2 g of the organosiloxane from Example 8b, 26.4 g of 1-(4'-allyloxybenzoyloxy)-4-(4"-(acryloyloxy)benzene from Example 4, 8.4 g of 2-[4'-(4"-acryloylbutoxy)benzoyl]-5-anisoylisosorbide from Example 10c and 1.2 g of Irgacure® 907 were dissolved in 500 ml of para-xylene, and the solution was filtered through a 0.45 µm membrane filter and freeze-dried.

The resultant mixture was applied in a layer thickness of about 15 µm to a polyethylene terephthalate film (Hostaphan@, obtainable from Hoechst-Diafoil GmbH, 65203 Wiesbaden) at 85° C. with the aid of a knife coater. The alignment of the liquid-crystalline molecules which was produced during application was fixed by irradiation for 5 seconds with a mercury vapor lamp (electrical output 80 W/cm).

The coating formed on the film was brittle both in the cold and hot states and had a green color when viewed perpendicularly which changed to blue with increasing viewing angle. The light transmitted and reflected by the film was measured in a spectrophotometer fitted with circular polarizers. A reflection band for right-handed helical light was detected at wavelength 558 nm.

Example 16

19.8 g of the organosiloxane from Example 5a, 10.56 g of bis-1,4-[4'-(4"-methacryloxybutoxy)benzoyloxy]benzene from Example 9c, 2.64 g of 2-[4'-(4'-acryloylbutoxy)benzoyl]-5-anisoylisosorbide from Example 10c, 10 mg of 2,6-di-t-butyl-4-(dimethylaminomethylene)phenol (Ethanox® 703) and 0.83 g of the photoinitiator phenyl-bis(2,4,6-trimethylbenzoyl)phosphine oxide (trademark Irgacure® 819 from Ciba Spezialitätenchemie Lampertheim GmbH, 68619 Lampertheim) were dissolved in 100 ml of toluene at 70° C. The solvent was removed to a residual content of less than 1% in a rotary evaporator. The liquid-crystalline mixture produced in this way had a glass transition temperature of −7° C. and a clearing point of 92° C.

This liquid-crystal material was applied in a layer thickness of 10 µm to a polyethylene terephthalate film (Hostaphan®) at 82° C. with the aid of a knife coater and crosslinked photochemically at 82° C. with the aid of a mercury vapor lamp (80 W/cm). This gave a film which was tack-free and brittle in the cold and hot states and whose color changed, independently of the temperature, from green to blue depending on the viewing angle. A piece of this film exhibited a reflection wavelength of 520 nm when viewed perpendicularly in a spectrophotometer.

A sample of this film was, after detachment of the support film, immersed in a toluene bath for 24 hours. After 2 hours, the sample was removed from the bath for the first time and the reflection wavelength checked. No change was observed. After 24 hours in the toluene bath, the sample was still mechanically stable. A slight shift in the reflection wavelength to 550 nm was measured. This was reversible after drying. After detachment of the LC film from the support film, comminution and subsequent grinding in a universal laboratory mill, particles down to a mean particle diameter of about 50 µm were produced. The pulverulent fraction obtained in this way was subsequently sieved using an analytical sieve having a mesh width of 50 µm and then incorporated into a conventional alkyd-melamine resin binder system (commercially available under the name Sacolyd F410/Sacopal M110 from Kolms Chemie, A-Krems). Using a thinner (mixture of aromatic hydrocarbons and methyl isobutyl ketone), the viscosity of the binder system was adjusted to an efflux time of about 80 seconds in a DIN-4 flow cup. The resultant mixture of LC platelets and binder was knife-coated in a wet-film thickness of 120 μm onto a black-primed metal sheet with the aid of a film applicator (manufacturer Erichsen). The sheet was subsequently dried at 80° C. for one hour. When viewed perpendicularly, the sheet exhibited a green color during and after drying, which changed to blue at flatter viewing angles. Selective reflection of right-handed helical light at wavelength 520 nm was detected when viewed perpendicularly in a spectrophotometer fitted with circular polarizers.

Comparative Example 17

A liquid-crystal mixture prepared as described in U.S. Pat. No. 5,211,877, Example 2b, was used to produce an aligned, polymerized film as described in Example 16 above. This film exhibited selective reflection of left-handed helical light at a wavelength of 530 nm when viewed perpendicularly in a spectrophotometer. After detachment of the support film, a sample of this film was immersed in a toluene bath. After a few minutes, the film broke up into whitish, cloudy flakes. Selective reflection of circular-polarized light was no longer observed, even after the flakes had been dried.

Comparative Example 18

32.0 g (0.1 mol) of 1-(4'-allyloxybenzoyloxy)-4-(4''-acryloyloxy)benzene from Example 4 and 6.0 g (0.02 mol) of pentamethylcyclopentasiloxane were dissolved in 110 ml of toluene, and 0.69 ml of a 1% strength hexachloroplatinic acid solution was added at 80° C. The reaction product could not be isolated any further since the solution solidified in a gelatinous manner.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A process for the preparation of organosilicon compounds (P) containing α,β-unsaturated carboxylic acid radicals, of the general formula (1)

—A—O—C(O)—CR=CH$_2$   (1), comprising reacting, in a first step, organosilicon compounds (H) containing hydrogen atoms bonded directly to silicon are reacted with olefinically unsaturated compounds (U) containing a terminal double or triple bond, of the general formula (2)

Ω-O—C(O)—CRH—CH$_2$—Z   (2), in the presence of metals or compounds from the platinum group as catalyst, to give organosilicon compounds (E) containing radicals of the general formula (3)

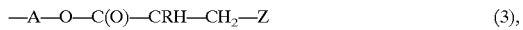
—A—O—C(O)—CRH—CH$_2$—Z   (3), and, in a second step, eliminating H—Z compounds from organosilicon compounds (E), where A is a divalent organic radical, Ω is a monovalent organic radical containing a terminal double or triple bond, R is an H atom or a methyl radical, and Z is Cl, I, Br or 4-methyltoluenesulfonyl.

2. The process of claim 1, wherein the H—Z compounds are eliminated by means of a base.

3. The process of claim 1, wherein the organosiloxanes (H) employed comprise at least 2 identical or different units of the general formula (4)

[H$_p$R$^1_q$SiO$_{(4-p-q)/2}$]   (4), in which

R$^1$ is a C$_1$- to C$_{10}$-alkyl or phenyl radical which is unsubstituted or substituted by halogen atoms, and p and q each have the value 0, 1, 2 or 3, where the sum of p and q is at most 3, and wherein at least one unit per molecule, p has the value 1, 2 or 3.

4. The process of claim 2, wherein the organosiloxanes (H) employed comprise at least 2 identical or different units of the general formula (4)

[H$_p$R$^1_q$SiO$_{(4-p-q)/2}$]   (4), in which

R$^1$ is a C$_1$- to C$_{10}$-alkyl or phenyl radical which is unsubstituted or substituted by halogen atoms, and p and q each have the value 0, 1, 2 or 3, where the sum of p and q is at most 3, and wherein at least one unit per molecule, p has the value 1, 2 or 3.

5. The process of claim 1, wherein the organosilanes (H) employed have the general formula (5)

H$_s$SiR$^2_t$   (5), in which

R$^2$ is a halogen atom or a C$_1$- to C$_{10}$-alkyl or phenyl radical which is unsubstituted or substituted by halogen atoms, s has the value 1, 2, 3 or 4, and t has the value 0, 1, 2, 3 or 4, where the sum of s and t is at most 4.

6. The process of claim 2, wherein the organosilanes (H) employed have the general formula (5)

H$_s$SiR$^2_t$   (5), in which

R$^2$ is a halogen atom or a C$_1$- to C$_{10}$-alkyl or phenyl radical which is unsubstituted or substituted by halogen atoms, s has the value 1, 2, 3 or 4, and t has the value 0, 1, 2, 3 or 4, where the sum of s and t is at most 4.

7. The process of claim 1, in which compounds (U) are employed in which, in the general formula (2), Ω is R$^3$—A$^0$, where R$^3$ is a monovalent radical of the formula CH$_2$=CH—(CH$_2$)n or HC≡C—(CH$_2$)$_n$, in which n is an integer having a value of from 0 to 8, and in which one or more non-adjacent methylene units may be replaced by oxygen atoms or dimethylsilyl radicals, and A$^0$ is a chemical bond or a divalent organic radical.

8. The process of claim 2, in which compounds (U) are employed in which, in the general formula (2), Ω is R$^3$—A$^0$, where $R^3$ is a monovalent radical of the formula $CH_2=CH-(CH_2)_n$ or $HC\equiv C-(CH_2)_n$, in which n is an integer having a value of from 0 to 8, and in which one or more non-adjacent methylene units may be replaced by oxygen atoms or dimethylsilyl radicals, and $A^0$ is a chemical bond or a divalent organic radical.

9. The process of claim 3, in which compounds (U) are employed in which, in the general formula (2), $\Omega$ is $R^3-A^0$, where $R^3$ is a monovalent radical of the formula $CH_2=CH-(CH_2)_n$ or $HC\equiv C-(CH_2)_n$, in which n is an integer having a value of from 0 to 8, and in which one or more non-adjacent methylene units may be replaced by oxygen atoms or dimethylsilyl radicals, and $A^0$ is a chemical bond or a divalent organic radical.

10. The process of claim 5, in which compounds (U) are employed in which, in the general formula (2), $\Omega$ is $R^3-A^0$, where $R^3$ is a monovalent radical of the formula $CH_2=CH-(CH_2)_n$ or $HC\equiv C-(CH_2)n$, in which n is an integer having a value of from 0 to 8, and in which one or more non-adjacent methylene units may be replaced by oxygen atoms or dimethylsilyl radicals, and $A^0$ is a chemical bond or a divalent organic radical.

11. The process of claim 7, in which $A^0$ is $(CRH)_m-$, where m is an integer having a value of from 0 to 12, and R is an H atom or a methyl radical, and where one or more non-adjacent methylene units may be replaced by oxygen atoms, dimethylsilyl radicals, 1,4-substituted phenylene or cyclohexylene units.

12. The process of claim 1, wherein liquid-crystalline organosiloxanes (P) are prepared by hydrosilylating mesogenic compounds onto the organosilicon compounds (H).

13. The process of claim 12, in which the mesogenic compounds are selected from compounds of the general formula (6)

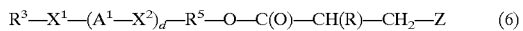

and compounds of the general formula (7)

where $R^3$ is a monovalent radical of the formula $CH_2=CH-(CH_2)_n$ or $HC\equiv C-(CH_2)_n$, in which n is an integer having a value of from 0 to 8, and in which one or more non-adjacent methylene units may be replaced by oxygen atoms or dimethylsilyl radicals, $R^5$ is a chemical bond or a radical of the formula $(CH_2)_m$, in which m is an integer having a value of from 1 to 12, and in which one or more non-adjacent methylene units may be replaced by oxygen atoms or dimethylsilyl radicals, $X^1$ is selected from a chemical bond and the divalent radicals $-O-$, $-C(O)O-$ and $-OC(O)-$, $X^2$ is a binding member selected from a chemical bond and the divalent radicals $-C(O)O-$, $-OC(O)-$, $-CH_2CH_2-$, $-CH=N-$, $-N=CH-$, $-N=N-$, $-C(O)NH-$, $-NHC(O)-$, $-C\equiv C-$, $-CH=CH-$, $-N=N(O)-$ and $-N(O)=N-$, $A^1$ is a divalent six-membered homocyclic or heterocyclic radical or bicyclic radical consisting of six-membered rings, optionally substituted by cyano, fluorine or methyl groups, $A^2$ is an end group selected from hydrogen, halogen, hydroxyl, nitrile, methacryloyloxy, methacryloylethyleneoxy, cholestane, cholesteryl, doristeryl, monofunctional dianhydrohexitol, cyclohexane and alkenyl radicals having 1 to 10 carbon atoms, in which one or more non-adjacent methylene units may be replaced by oxygen or dimethylsilyl radicals, and d can have the value 2 or 3.

14. The process of claim 13, wherein said six-membered homocyclic or heterocyclic radical comprises a ring selected from the group consisting of 1,4-phenylene, 1,4-cyclohexylene, 2,5-pyridinylene, 2,5-pyranylene, 2,5-pyrimidinylene, 5,2-pyrimidinylene, 2,5-(1,3-dioxanylene) and 5,2-(1,3-dioxanylene), and wherein said bicyclic radical comprises a radical selected from the group consisting of 2,6-naphthylidene, 2,7-naphthylidene and 1,4-naphthylidene.

15. A composition comprising organosilicon compounds (P) prepared by the process of claim 1.

16. A composition comprising organosilicon compounds (P) prepared by the process of claim 3.

17. A composition comprising organosilicon compounds (P) prepared by the process of claim 5.

18. A polymer prepared by polymerizing composition comprising at least one organosilicon compound (P) prepared by the process of claim 1.

19. An optically anisotropic layer produced by aligning and polymerizing a polymerizable composition comprising at least one liquid-crystalline organosilicon compound(P) prepared by the process of claim 1.

* * * * *